US009671360B2

(12) United States Patent
Shin et al.

(10) Patent No.: US 9,671,360 B2
(45) Date of Patent: Jun. 6, 2017

(54) BIOSENSOR AND METHOD FOR MANUFACTURING SAME

(75) Inventors: Heung Joo Shin, Ulsan (KR); Jeong Il Heo, Yongin-si (KR); Yeong Jin Lim, Busan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 302 days.

(21) Appl. No.: 14/369,199

(22) PCT Filed: Apr. 2, 2012

(86) PCT No.: PCT/KR2012/002444
§ 371 (c)(1),
(2), (4) Date: Jun. 27, 2014

(87) PCT Pub. No.: WO2013/100264
PCT Pub. Date: Jul. 4, 2013

(65) Prior Publication Data
US 2014/0353152 A1 Dec. 4, 2014

(30) Foreign Application Priority Data

Dec. 29, 2011 (KR) ........................ 10-2011-0146152

(51) Int. Cl.
*G01N 27/30* (2006.01)
*G01N 27/327* (2006.01)
(52) U.S. Cl.
CPC ....... *G01N 27/308* (2013.01); *G01N 27/3278* (2013.01)

(58) Field of Classification Search
CPC ........... B81C 1/0019; B82B 1/00; B82B 3/00; B82Y 30/00; B82Y 40/00; G01N 27/127;
(Continued)

(56) References Cited

U.S. PATENT DOCUMENTS 5,632,085 A * 5/1997 Tegeder .................. A61N 1/05
156/86
7,682,659 B1 3/2010 Wang et al.
(Continued)

FOREIGN PATENT DOCUMENTS

JP 2009-288080 A 7/2011

*Primary Examiner* — Sally Merkling
(74) *Attorney, Agent, or Firm* — Revolution IP, PLLC

(57) ABSTRACT

Disclosed is a method for manufacturing a biosensor comprising (a) forming an insulating layer in an electrode region; (b) coating the first photoresist layer on the insulating layer; (c) performing the first exposing process on the first electrode region through the first photomask; (d) removing unexposed area of the first photoresist layer except for the first electrode region using development; (e) coating the second photoresist layer on the first electrode region and the insulating layer after the step (d); (f) performing the second exposing process on the second electrode regions through the second photomask; (g) performing the third exposing process on the top portion of the second photoresist layer through a photomask with open areas in the shape of micro-sized wires connecting the second electrode regions; (h) removing the second photoresist layer except for the portions exposed in the steps (c), (f) and (g) using development.

6 Claims, 4 Drawing Sheets

(58) Field of Classification Search
CPC .............. G01N 27/4146; G01N 27/308; G01N 27/3278; G03F 7/40; G03F 7/70466; H01J 37/3174; G21K 1/062; H01L 21/0337; H01L 21/3086; H01L 21/31144; H01L 21/76816
See application file for complete search history.

(56) References Cited

U.S. PATENT DOCUMENTS

2002/0179434 A1* 12/2002 Dai .................... B82B 1/00
204/242
2004/0100269 A1  5/2004 Cole et al.

\* cited by examiner

BIOSENSOR AND METHOD FOR MANUFACTURING SAME

CROSS REFERENCE TO PRIOR APPLICATIONS

This application is a National Stage Application of PCT International Patent Application No. PCT/KR2012/002444 filed on Apr. 2, 2012, under 35 U.S.C. §371, which claims priority to Korean Patent Application No. 10-2011-0146152 filed on Dec. 29, 2011, which are all hereby incorporated by reference in their entirety.

TECHNICAL FIELD

The present invention relates to a biosensor and a method for manufacturing the same, and more particularly, to a biosensor that senses a specific biomaterial through an overlapped carbon micro/nano structures, and a method for manufacturing the same.

BACKGROUND ART

In recent years, growing interests in environmental issues with the development of data communication equipments have given rise to the development of a variety of sensors for detectin and monitoring biomaterials. And by using semicondutor technologies, the manufacturing process of sensors becomes simple and their performance becomes enhanced. The approach to improve the performance of sensors (e.g. sensitivity) are actively researched in various fields.

Electrochemical sensors and optical sensors are most widely used as biosensing mechanism.

Optical sensors show very fast response on the target analytes and high sensitivity. However, their relatively complex configuration and bulky size limit space utilization and efficient operation.

The limitations of the optical sensors listed above can be overcome by using electrochemical sensing mechanism. The electrochemical sensors measure electrochemical currents flowing through external circuits that are generated in oxidation and reduction reactions of analytes. And the electrochemical sensors also use electromotive force generated at ion electrodes by ions in electrolytes, ionized gases, ions dissolved in solid. However, relatively low sensitivity and slow response time compared to the optical sensors limits extension of their applications.

In the Korean Patent (Registration No. 0741187), an electrochemical sensor that measures a concentration of an analyte measures a concentration of an analyzing target component in an aqueous liquid sample by placing the sample in an electrochemical cell including two electrodes with some impedeance that allow current measurement. By directly or indirectly reacting the analyzing target materials with an oxidation and reduction agent, a material that can be oxidized or reduced is formed to have the amount corresponding to the concentration of the analyzing target component. Subsequently, the amount of the material that can be oxidized or reduced is electrochemically measured. In the aforementioned method, the electrodes need to be sufficiently separated from each other so as not to allow electrochemical products at on electrode to reach the other electrode and thus interference between two electrodes can be minimized during the measurement. Furthermore, manufacturing cost may be high, and a manufacturing process may be complex.

DISCLOSURE

Technical Problem

An objective of the present invention is to provide a biosensor with reduced size and improved sensitivity by improving a structure of the biosensor, and to provide a method for manufacturing the same.

An objective of the present invention is also to provide a method for manufacturing a biosensor composed of carbon micro/nanowires and controlling their geometries including numbers, position and morphology in a designed manner. As a result, it is possible to produce the carbon-micro/nano-wire-based biosensors at a low producing cost with mass-production using the method.

Technical Solution

An exemplary embodiment of the present invention provides a method for manufacturing a biosensor. The method includes (a) forming an insulating layer in an electrode region including the first electrode region and a plurality of the second electrode regions on a substrate; (b) coating the first photoresist layer on the insulating layer; (c) performing the first exposing process on the first electrode region through the first photomask; (d) removing unexposed area of the first photoresist layer except for the first electrode region using development; (e) coating the second photoresist layer on the first electrode region and the insulating layer after the step (d); (f) performing the second exposing process to form the second electrode regions through the second photomask; (g) performing the third exposing process on the top portion of the second photoresist layer through a photomask with open areas in the shape of micro-sized wires connecting the second electrode regions; (h) removing the second photoresist layer except for the portions exposed in the steps (c), (f) and (g) using development; and (i) pyrolyzing the first and second electrode regions and the wires to form carbon electrodes and carbon wires.

Through the aforementioned method, it is possible to provide a biosensor composed of carbon micro/nano structures with improved sensitivity and reduced size and volume.

In the step (g), the first electrode region may be formed below the wire connecting the second electrode regions. The formed first electrode region may serve as oxidation electrode, and the second electrode regions and the carbon wire may serve as a reduction electrode. Further, the first electrode region may serve as a reduction electrode, and the second electrode regions and the carbon wire may serve as an oxidation electrode.

In the step (i), the carbon wires may have a mesh shape or a honeycomb shape. Since oxidation and reduction reactions of a biomaterial can be recycled between the formed carbon wire and the second electrodes, and the first electrode, it is possible to improve the sensitivity of the biosensor.

In the step (i), the width of the carbon wire may range from 30 nm to 900 µm, the separation of the carbon wire from the substrate may range from 100 nm to 900 µm, and the length of the carbon wire may range from 1 µm to 900 µm. Here, in the step (i), the carbon wire may be formed through the pyrolysis process, and the volume of the photoresist may be reduced through pyrolysis. Accordingly, a photoresist wire structure at microscale may be converted into various sizes of carbon wires depending on the conditions in pyrolysis including process time, temperature, heating speed, cooling speed, and gases.

Meanwhile, another exemplary embodiment of the present invention provides a method for manufacturing a biosensor. The method includes (a) preparing a substrate that includes the first electrode region and a plurality of second electrode regions and the substrate made of an insulating material; (b) coating the first photoresist layer on the substrate; (c) performing the first exposing process on the first electrode region through the first photomask; (d) removing unexposed area of the first photoresist layer except for the first electrode region using development; (e) coating the second photoresist layer on the first electrode region and the substrate after the step (d); (f) performing the second exposing process to form the second electrode regions through the second photomask; (g) performing the third exposing process on the top portion of the second photoresist layer through a photomask with open areas in the shape of micro-sized wires connecting the second electrode regions; (h) removing the second photoresist layer except for the portions exposed in the steps (c), (f) and (g) using development; and (i) pyrolyzing the first and second electrode regions and the wires to form carbon electrodes and carbon wires. As stated above, since the substrate is made of an insulating material, it is not necessary to form an additional insulating layer.

Meanwhile, still another exemplary embodiment of the present invention provides a biosensor including the first carbon electrode that is provided on a silicon substrate; second carbon electrodes that are separated from the first carbon electrode with a predetermined distance, and are provided along an outer periphery of the first carbon electrode; and carbon wires that connects upper portions of the second carbon electrodes and is provided on the first carbon electrode. In such a configuration, the size of the sensor is reduced, and its sensitivity is improved.

Advantageous Effects

A biosensor and a method for manufacturing the same according to the present invention have the following effects.

Firstly, it is possible to simply produce the overlapped carbon wire and carbone electrodes through the first, second and third exposing processes and the development process using batch processes at low cost.

Secondly, since the carbon wire is formed to be overlapped above the first electrode, the efficiency of the repeated reactions of the oxidation and reduction of a biomaterial can be improved and thus the sensitivity of the biosensor can be enhanced.

Thirdly, since the carbon wires can be formed in a linear, mesh or honey comb shape, materials that can be oxidized and reduced can be efficiently supplied to the electrode regions through empty spaces in the carbon wire.

Fourthly, since the shape of the carbon wire is determined by the shape of the photomask, the amount of exposed energy and the pyrolysis process, and the distance between the carbon wire and the substrate is determined by the height of the photoresist layer and the pyrolysis process, it is possible to freely pattern various shapes of overlapped carbon wire structures.

Fifthly, since the carbon wire structure is formed by reducing the volume of the micro-sized photoresist through pyrolysis, it is possible to produce nano-sized structures at low cost without using expensive nano-fabrication equipments.

Sixthly, the carbon electrode-based sensors manufactured by the present manufacturing method can be widely used to sense any material that can be oxidized and reduced as well as biomaterials.

Seventhly, since the volume of the carbon structures is reduced through pyrolysis, the volumes of upper regions of the second carbon electrodes are reduced and as a result tension may be developed along the carbon wire connecting both the ends of the second carbon electrodes. Such tension can prevent the carbon wire from breaking down and sticking to the substrate that can be caused by the surface tension when the carbon wire is used in liquid phase.

BEST MODE

Figure 1:
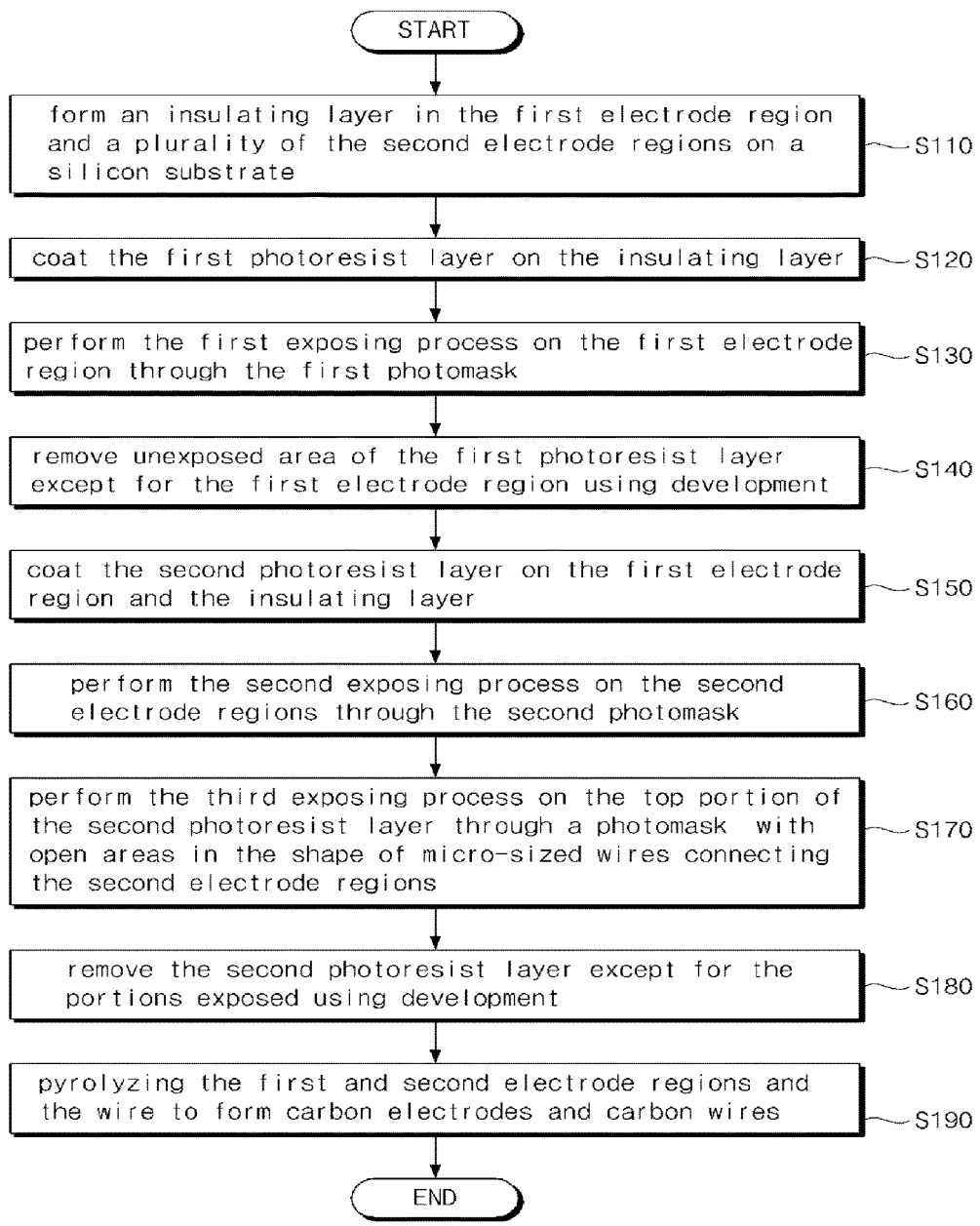
FIG. 1 is a flowchart illustrating a method for manufacturing a biosensor according to the embodiment of the present invention.

Hereinafter, preferred embodiments of the present invention will be described in detail with reference to the accompanying drawings. Prior to the description, it should be understood that the terminologies and terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation.

Accordingly, embodiments described in the specifications and configurations illustrated in the drawings are merely the most preferred embodiments of the present invention, and do not wholly represent the technical sprit of the present invention. Therefore, it should be appreciated that various modifications and equivalents to these embodiments are possible at the time of filing the present application.

Hereinafter, preferred embodiments of the present invention will be described in detail with reference to the accompanying drawings.

Figure 2:
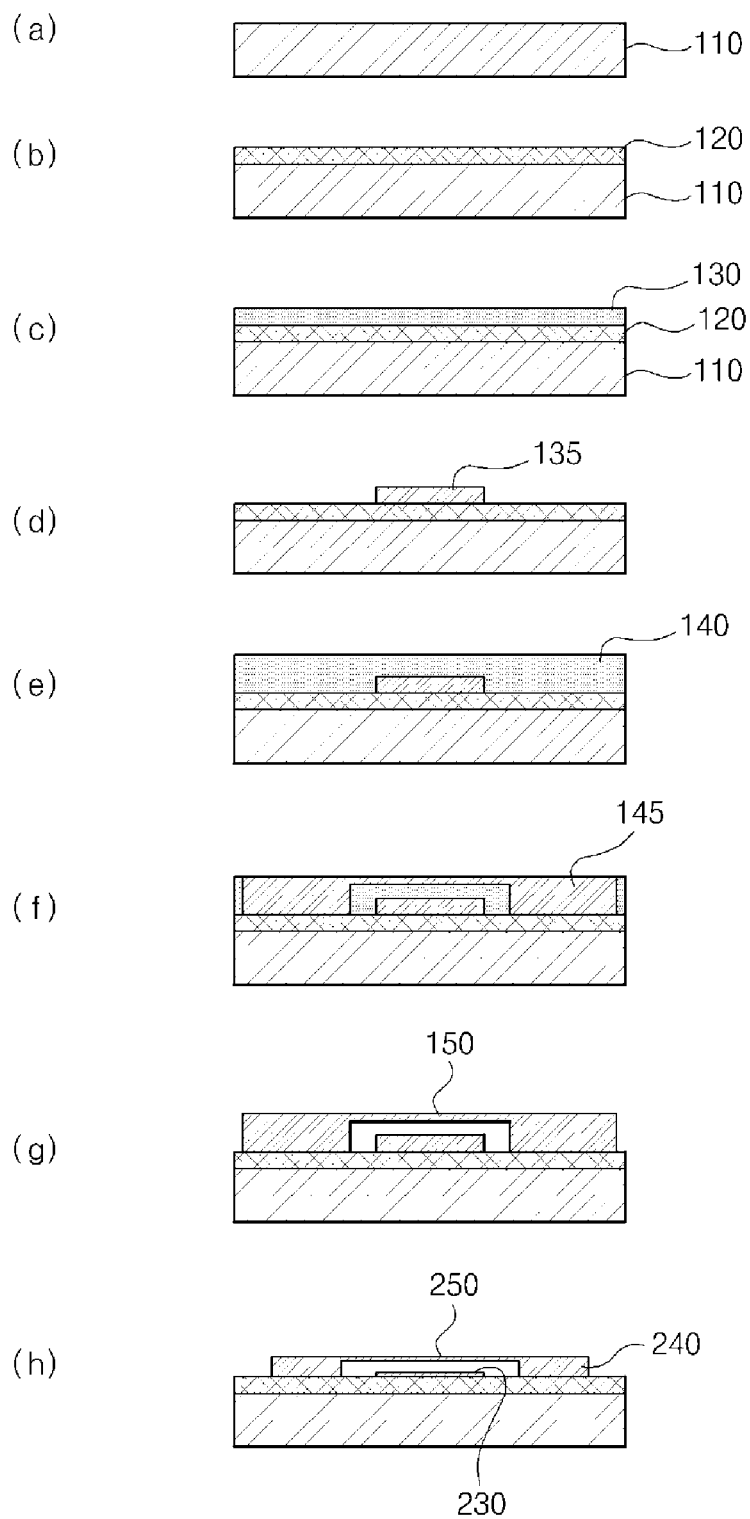
FIG. 2 is a process diagram for describing the method for manufacturing a biosensor of FIG. 1.
Figure 3:
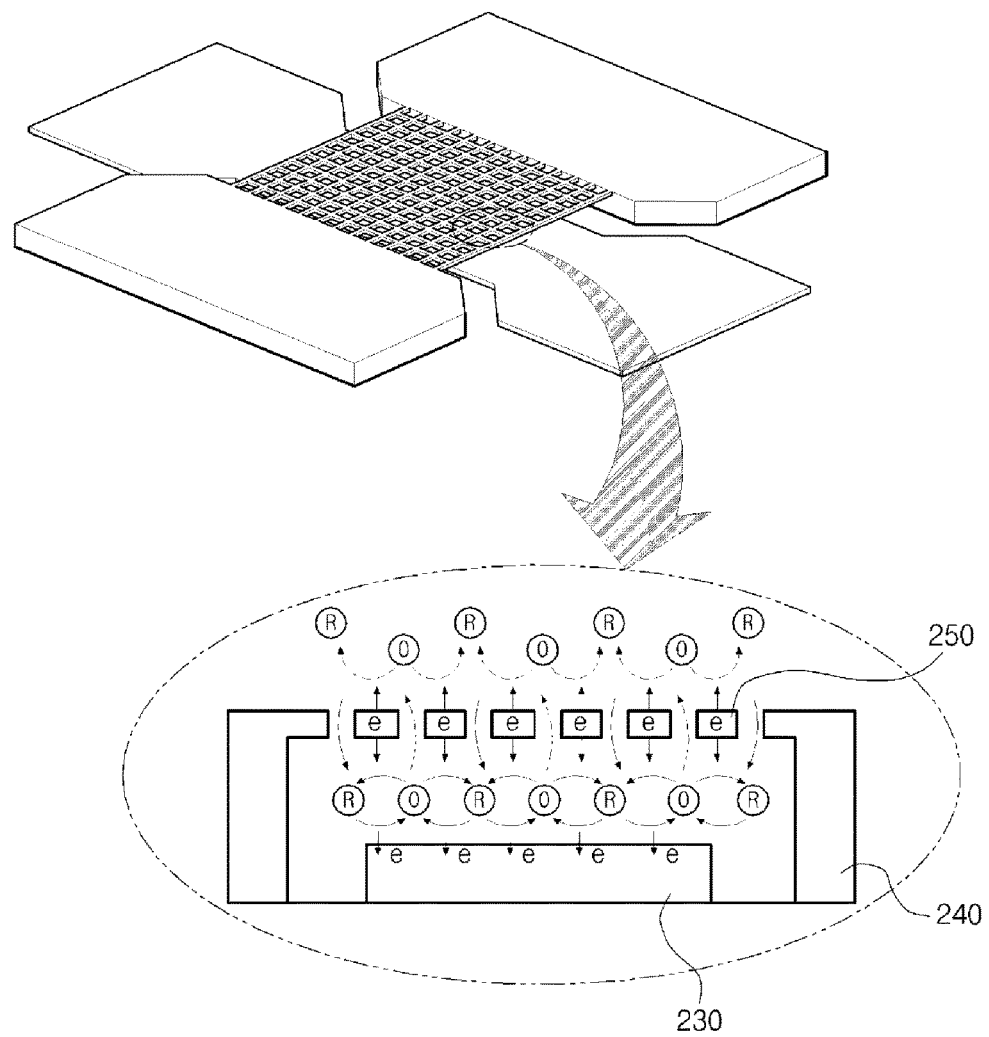
FIG. 3 is an enlarged view of the biosensor of FIG. 1.
Figure 4:
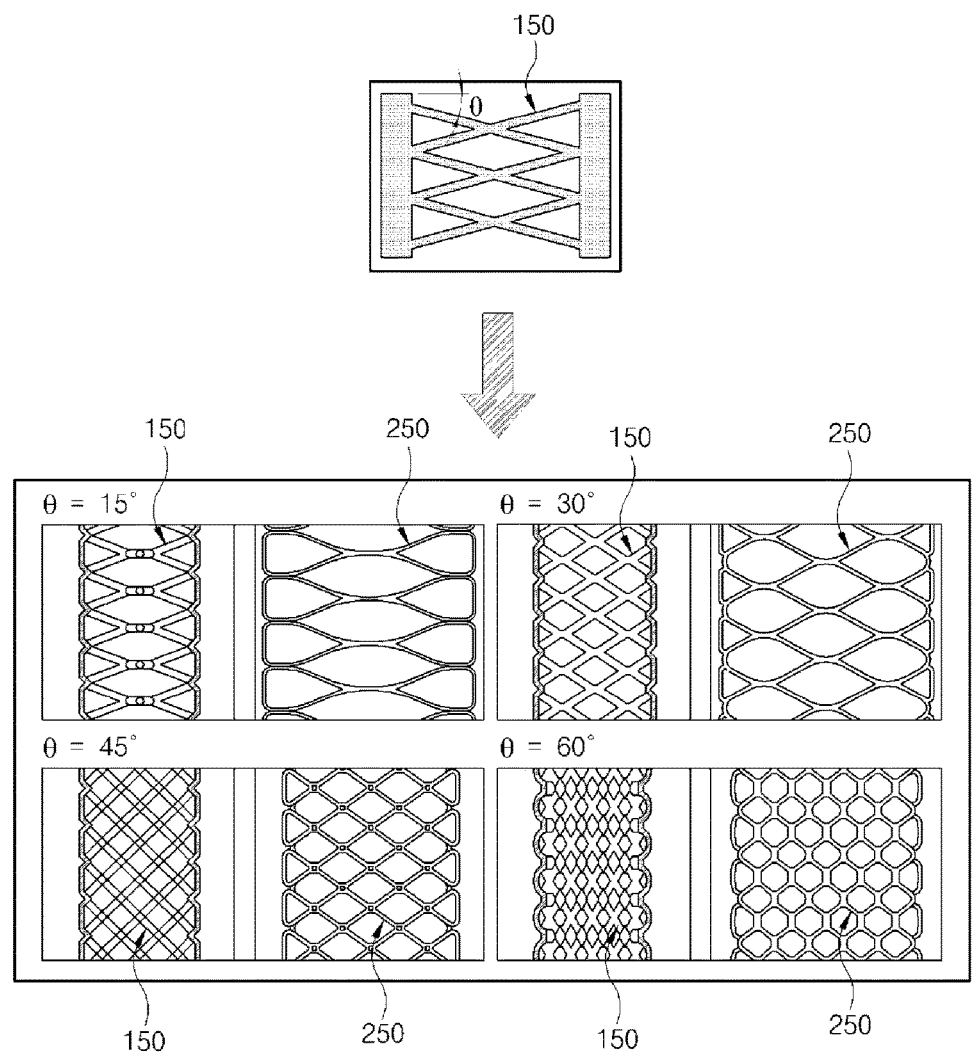
FIG. 4 illustrates the biosensor of FIG. 1 depending on pyrolysis conditions.

FIG. 1 is a flowchart illustrating a method for manufacturing a biosensor according to the embodiment of the present invention, FIG. 2 is a process diagram for describing the method for manufacturing a biosensor of FIG. 1, FIG. 3 is an enlarged view of an overlapped carbon-micro/nano-structured biosensor of FIG. 1, and FIG. 4 is a diagram illustrating the overlapped carbon-micro/nano-structured biosensor before and after pyrolysis.

Referring to FIGS. 1 and 2, the method for manufacturing a biosensor according to the embodiment of the present invention includes step S110 of forming an insulating layer in an electrode region including the first electrode region and a plurality of second electrode regions on the silicon substrate, step S120 of coating the first photoresist layer on the insulating layer, step S130 of performing the first exposing process on the first electrode region through the first photomask, step S140 of removing the photoresist layer except for the first electrode region using development, step S150 of coating the second photoresist layer on the first electrode region and the other region, step S160 of performing the second exposing process on the second electrode regions through the second photomask, step S170 of performing the third exposing process on the top portion of the second photoresist through a photomask with open areas in the shape of micro-sized wires connecting the second electrode regions, step S180 of removing the second photoresist layer except for the regions exposed in the first, second and third exposure processes using development, and step S190 of pyrolyzing the first and second electrode regions and the wire to form overlapped carbon electrodes and carbon wires.

In step S110 of forming an insulating layer in the electrode regions including the first electrode region and a plurality of the second electrode regions on the silicon substrate, the primary insulating layer 120 is first formed on the entire top surface of the silicon substrate 110. The primary insulating layer is made of insulating materials such as silicon dioxide, silicon nitride, etc.

Although the substrate made of silicon has been used in the present embodiment, the substrate may be made of other materials other than silicon as long as an insulating layer can be formed on the substrate.

Furthermore, although the insulating layer has been formed on the silicon substrate in the present embodiment, the step of forming the insulating layer may be omitted and the substrate may be made of an insulating material.

When the insulating layer 120 is formed, step S120 of primarily coating a photoresist on the insulating layer 120 is performed. Thereafter, the first exposing process of exposing a photoresist 130 through the first photomask to ultraviolet light to form the first electrode region is performed (S130). When the first exposing process is finished, the photoresist may be cured in an electrode shape to form the first electrode region 135 on the primary insulating layer. At this time, exposed light energy needs to be sufficient to cure the photoresist from the uppermost portion of the photoresist to a portion directly on the primary insulating layer.

When the first exposing process is finished, the photoresist portion except for the first electrode region may be removed using development (S140). After the photoresist portion except for the first electrode region is removed using development, the second photoresist 140 may be coated on the first electrode region and the region where the second electrode region is to be formed (S150).

Subsequently, a step of performing the second exposing process on the second electrode regions through the second photomask to form the second electrode regions is performed (S160). In step S160 of performing the second exposing process, energy of ultraviolet light to be absorbed into the photoresist needs to be sufficient to cure the photoresist from the uppermost portion of the photoresist 140 to a portion directly on the primary insulating layer.

As described above, when the second exposing process is finished, step S170 of performing the third exposing process on the top portion of the second photoresist layer through a photomask with open areas in the shape of micro-sized wires connecting the second electrode regions is performed. The third exposing process can polymerize only photoresist uppermost regions by using lower exposure energy than those in the first and second exposures processes. A part of the photoresist connecting the second electrode regions 145 is polymerized into the wire shape through the third exposing process to form micro photoresist wires 150 connecting the second electrode regions. At this time, the first electrode region 135 may be formed below the wire 150 connecting the second electrode regions 145, and the first electrode region 135 and the wire 150 may be formed so as to be separated with a predetermined distance.

After the third exposing process is finished, the step of removing the photoresist except for the portions exposed in the first, second and third exposing processes using development (S180). When the photoresist that is not exposed in the first, second and third exposing processes is removed using development, the photoresist in the region between the first electrode region and the wire 150 is removed (S180). Through this process, only the first electrode region 135, the second electrode regions 145 and the micro photoresist wire 150 remain.

Meanwhile, in the embodiment of the present invention, the photoresist used in the first, second and third exposing processes may be negative photoresists including SU-8 photoresist, and the present invention is not limited or restricted by the kind of the photoresist.

The first electrode region 135, the second electrode regions 145 and the wire 150 may be formed as the micro- or nano-sized carbon structure through pyrolysis (S190). To achieve this, the pyrolysis process may be performed at a high temperature of 800° C. or more in a vacuum condition or an inert gas environment. Through the pyrolysis, the first electrode region 135, the second electrode regions 145 and the wire 150 may be converted into carbon wires 250, the first carbon electrode 230, and second carbon electrodes 240 that accommodate the first carbon electrode 230.

That is, referring to FIG. 3, the biosensor formed by the method for manufacturing a biosensor includes the first carbon electrode 230, the second carbon electrodes 240, and the carbon wire 250.

The biosensor formed through pyrolysis may have a width ranging from 30 nm to 10 μm, a separation from the substrate ranging from 100 nm to 10 μm, and a length ranging from 1 μm to 900 μm. In the pyrolysis process, the volume of the wire is reduced, and the size of the photoresist wire may be reduced to nanometer-scale.

At this time, the carbon wire 250 may be formed in a mesh shape or a honeycomb shape. Since the carbon wire 250 is formed in the mesh shape or the honeycomb shape, biomaterials can be efficiently supplied to the primary carbon electrode 230 and the second carbon electrode, the area for the oxidation and reduction reactions is increased, and the efficiency of oxidation-reduction recycling reaction is improved and thus the sensitivity of the biosensor can be enhanced. Here, the carbon wire 250 and the second carbon electrodes 240 may act as oxidation electrodes that oxidize the biomaterial, and the first carbon electrode 230 may act as a reduction electrode that reduces the biomaterial. Alternatively, the carbon wire 250 and the second carbon electrodes 240 may act as reduction electrodes that reduce the biomaterial, and the first carbon electrode 230 may act as an oxidation electrode that oxidizes the biomaterial.

Moreover, since the carbon wire structure is formed by reducing the volume thereof through pyrolyzing the micro-sized photoresist structure, it is possible to produce nano-sized structures at low cost without using expensive nano-fabrication equipments.

Meanwhile, a shape of the carbon structure may be changed depending on the pyrolysis conditions in the pyrolysis process. That is, referring to FIG. 4, assuming the angle between diagonal lines of the carbon wires 250 is 2θ, the final shape of the carbon wire can be changed depending on the change in the angle θ and the pyrolysis conditions. For example, the θ may be 10° to 70°, and it can be seen that as the size of θ is increased, the shape of the mesh becomes changed into more circular shape.

The sensitivity of the biosensor is controlled by controlling efficiency of the oxidation and reduction reactions of the biomaterial through changing the shape of the carbon wire 250. And the number of recycling oxidation and reduction reactions can be modulated by controlling the distance between the carbon wire and the first carbon electrode.

The present invention has been described in connection with the embodiments illustrated in the drawings, but the embodiments are merely examples. It should be understood to those skilled in the art that various modifications and equivalents to these embodiments are possible. Therefore, the technical scope should be defined by the technical spirit of the appended claims.

The invention claimed is:

1. A method for manufacturing a biosensor, comprising:
   forming an insulating layer on a substrate;
   coating a first photoresist on the insulating layer;
   exposing a first electrode region of the first photoresist to ultraviolet light through a first photomask;
   forming the first electrode region on the insulating layer by removing the first photoresist unexposed to ultraviolet light using development;
   coating a second photoresist on the first electrode region and the insulating layer;
   exposing a plurality of second electrode regions of the second photoresist to ultraviolet light through a second photomask;
   exposing a portion of the second photoresist which connects the second electrode regions to ultraviolet light through a third photomask in the shape of micro-sized wires;
   forming the second electrode regions, and the micro-sized wires connecting the second electrode regions by removing the second photoresist unexposed to ultraviolet light; and
   pyrolyzing the first electrode region, the second electrode regions and the micro-sized wires to form carbon electrodes and carbon wires.

2. The method for manufacturing a biosensor of claim 1, wherein the first electrode region is formed below the micro-sized wires connecting the second electrode regions.

3. The method for manufacturing a biosensor of claim 1, wherein the carbon wires have a mesh shape or a honey comb shape.

4. The method for manufacturing a biosensor of claim 1, wherein the first photoresist and the second photoresist are SU-8.

5. The method for manufacturing a biosensor of claim 1, wherein a width of the carbon wires ranges from 30 nm to 10 µm, a height of the carbon wires from the substrate ranges from 100 nm to 10 µm, and a length of the carbon wires ranges from 1 µm to 900 µm.

6. A method for manufacturing a biosensor, comprising:
   preparing a substrate made of an insulating material;
   coating a first photoresist on the substrate;
   exposing a first electrode region of the first photoresist to ultraviolet light through a primary photomask;
   developing the first photoresist unexposed to ultraviolet light to form the first electrode region on the substrate;
   coating a second photoresist on the first electrode region and the substrate;
   exposing a plurality of second electrode regions of the second photoresist to ultraviolet light through a second photomask;
   exposing a portion of the second photoresist which connects the second electrode regions to ultraviolet light through a third photomask in the shape of micro-sized wires;
   forming the second electrode regions, and the micro-sized wires connecting the second electrode regions by removing the second photoresist unexposed to ultraviolet light; and
   pyrolyzing the first electrode region, the second electrode regions and the micro-sized wires to form carbon electrodes and carbon wires.

\* \* \* \* \*